(12) United States Patent
Takvoryan (10) Patent No.: US 7,964,149 B1
(45) Date of Patent: Jun. 21, 2011

(54) CEMETERY INCENSE BURNER

(76) Inventor: Vahan Takvoryan, Van Nuys, CA (US)

( * ) Notice: Subject to any disclaimer, the term of this patent is extended or adjusted under 35 U.S.C. 154(b) by 893 days.

(21) Appl. No.: 11/880,397

(22) Filed: Jul. 19, 2007

Related U.S. Application Data (60) Provisional application No. 60/833,964, filed on Jul. 29, 2006, provisional application No. 60/859,429, filed on Nov. 15, 2006.

(51) Int. Cl.
*F23Q 2/32* (2006.01)
(52) U.S. Cl. .................................................. 422/126
(58) Field of Classification Search ............... 47/41.1, 47/41.14; 431/127; D11/131.1; 422/126
See application file for complete search history.

(56) References Cited

U.S. PATENT DOCUMENTS

| | | | |
|---|---|---|---|
| D56,810 S | 12/1920 | Halstead | |
| D61,140 S | 6/1922 | Lucas | |
| 2,276,749 A * | 3/1942 | Vanderveer | 47/41.1 |
| 2,676,434 A * | 4/1954 | Carlson | 47/41.1 |
| 3,328,914 A * | 7/1967 | Newman | 47/41.1 |
| D245,992 S | 10/1977 | Gruber | |
| D250,417 S | 11/1978 | Preston | |
| 4,155,979 A | 5/1979 | Powell | |
| D255,708 S | 7/1980 | Allen et al. | |
| 4,217,729 A | 8/1980 | Cooper | |
| D264,869 S | 6/1982 | Gordon | |
| 4,347,217 A | 8/1982 | Radkins et al. | |
| 4,631,859 A | 12/1986 | Letter et al. | |
| 4,722,160 A | 2/1988 | Davis | |
| 4,909,235 A * | 3/1990 | Boetcker | 126/9 R |
| 5,215,719 A | 6/1993 | Newman | |
| D343,807 S | 2/1994 | Newman et al. | |

(Continued)

OTHER PUBLICATIONS

G.F.D. Imports, G.F.D. Imports Wild Berry Incense Distributor, webpage www.incensewholesale.com/burners/main.htm, 4 pages, printed Sep. 9, 2006.

*Primary Examiner* — Walter D Griffin
*Assistant Examiner* — Timothy Cleveland
(74) *Attorney, Agent, or Firm* — Law Offices of David L. Hoffman (57) ABSTRACT

The apparatus is a cemetery incense burner having a removable resin incense holder retained in a container for accommodating the incense holder. The top and bottom sections of the removable incense holder serve two separate functions. The top concave surface of the removable incense holder is used as a censer for burning incense when inserted into the container in a right side up position. The container has a protrusion in a bottom center thereof to support the removable incense holder and to allow it to rise above the surface of the ground while it is being used as a censer. The bottom surface of the removable incense holder forms a seal with the top of the container and has a built in handle for easy removal when placed upside down (censer side down) in the container for storage. In another embodiment, the container has a flat bottom so that the holder is flush with the surface of the ground and container even in the use position. The container also has vertical recesses in its inner periphery for receiving projections from the periphery of the bottom of the holder to center the holder in the use position and provide a place to grip the holder when in the use position, and to accommodate the projections for forming the seal at the top of the container when the holder is in the storage position. In a further embodiment, the incense holder has a stick incense retaining member for holding stick incense.

15 Claims, 9 Drawing Sheets

U.S. PATENT DOCUMENTS

| | | |
|---|---|---|
| 5,563,981 A | 10/1996 | Hsiao |
| D377,917 S | 2/1997 | Bishop |
| D395,846 S | 7/1998 | Taylor |
| 6,119,394 A | 9/2000 | Fowler |
| D444,732 S | 7/2001 | McLeish et al. |
| 6,447,732 B1 | 9/2002 | West |
| 6,495,107 B2 | 12/2002 | Gaines |
| D480,324 S | 10/2003 | Stanley, III |
| D480,985 S | 10/2003 | Stanley, III |
| 6,846,462 B2 | 1/2005 | Stanley, III |
| D511,995 S | 11/2005 | Pettis, III |
| 2003/0231991 A1 | 12/2003 | Stanley, III |
| 2004/0136888 A1 | 7/2004 | Shimizu et al. |
| 2005/0260105 A1 | 11/2005 | Xu |

\* cited by examiner

CEMETERY INCENSE BURNER

CROSS REFERENCE TO RELATED APPLICATION(S)

This application claims priority from U.S. Provisional Patent Application Ser. No. 60/833,964 filed Jul. 29, 2006, and U.S. Provisional Patent Application Ser. No. 60/859,429 filed Nov. 15, 2006, both of which are incorporated by reference herein.

BACKGROUND OF THE INVENTION

1. Field of the Invention

The present invention relates to an incense burner for use at a grave site at a cemetery.

2. Description of the Related Art

In many cultures, burning incense has spiritual and religious connotations. In such cultures, burning incense at a cemetery allows prayers for persons that have passed away to infuse upwards towards the sky. The burning of incense is also intended to release fragrant smoke as it smolders for other religious purposes.

Resin incense is burned on small charcoal bricks (briquettes). In use, typically one lights the corner of a briquette, then places the lit brick in the censer (container for burning incense). One then extinguishes any flame. After the glowing sparks traverse the entire briquette, it is ready to have incense placed on it. Resin incense is the most common form of incense traditionally used for religious purposes. The resin incense is placed on the briquette and as the resin burns, the incense is released as smoke.

Currently, those wishing to burn incense at a cemetery for persons that have passed away, either bring their own incense burners to the cemetery and take the incense burner away when they are done or create an incense burner from aluminum foil and leave the incense burning in the aluminum foil next to a grave marker when they leave. This common practice creates a fire hazard for the cemetery as well as undue litter.

Therefore, there is a need for a device that allows an incense burner to be placed at a grave marker permanently. The device also needs to keep the incense burner from being damaged by wind, rain, and other perils associated with cemeteries, such as maintenance equipment and at the same time not to interfere with normal cemetery maintenance.

SUMMARY OF THE INVENTION

In one embodiment, there is a cemetery incense burner which would be inserted into the ground at a grave site near a grave marker. The cemetery incense burner has a resin incense holder and a container for accommodating the resin incense holder. The container is preferably of a geometric cross sectional shape that matches the cross sectional shape of the holder at the holder's widest portion. Preferably, the holder has a round section and so preferably the container is cylindrical.

At the top of the holder there is a concave section used as a censer for burning incense when inserted into the container. The container has a protruding metal portion in the bottom center thereof to support the removable incense holder and to allow it to rise above the surface of the ground while it is being used as a censer. At the bottom of the holder is an enclosure top with a handle for easy removal which when stored in the container is flush with the top of the container, which preferably is placed in the ground and is flush with or substantially flush with the surface of the ground so that the container and incense holder do not interfere with normal cemetery maintenance, such as cutting grass.

In a second embodiment of the incense holder and container, the holder is similar to that of the first embodiment. The container, however, has a flat bottom so that the holder, when in the use position, is also flush with the top of the container. In such a case, there preferably are recesses along the inside of the container, to provide access or clearance for tabs in the top of the holder and projections at the bottom of the holder when the holder is in the use or storage position.

In another embodiment, there is a stick incense holder fixed in the censer.

DESCRIPTION OF THE PREFERRED EMBODIMENT(S)

A first embodiment of a removable resin incense holder retained in a container for accommodating the incense holder is shown in FIGS. 1A to 1F.

The removable resin incense holder and the container can be made of any known material that can be used for creating such a removable resin incense holder and container. Exemplary materials are typically metals, such as brass, copper, bronze and any other suitable materials to provide strength and longevity. For example, ceramics may be used but care must be taken not to break them.

Figure 1A:
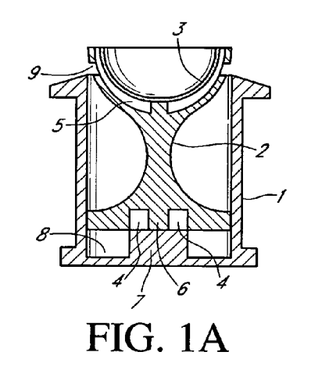
FIG. 1A is a vertical sectional view of an incense holder and container in a use position in accordance with a first embodiment of the invention.

In this first embodiment, the incense burner has a resin incense holder 2, preferably somewhat cup-shaped, and a container 1. Holder 2 is vertically slidable within container 1. The inside dimension of the container is sufficient by a relatively small clearance to accommodate the holder 2.

Figure 1B:
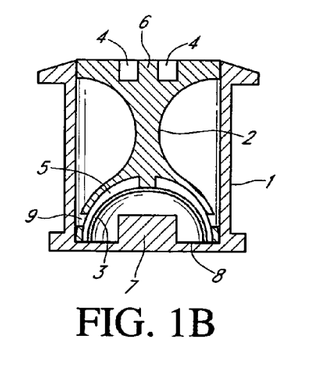
FIG. 1B is a vertical sectional view of the incense holder and container of FIG. 1A in a storage position.
Figure 1C:
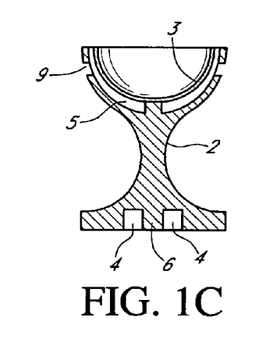
FIG. 1C is a vertical sectional view of the incense holder of FIG. 1A.
Figure 1D:
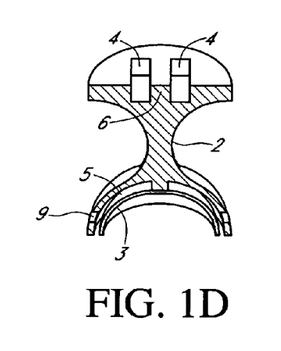
FIG. 1D is a perspective view of the incense holder of FIG. 1A, with the holder sliced vertically, and in the storage position of FIG. 1B.

A grave site visitor would arrive at the grave, where holder 2 is upside down in container 1 during nonuse, as shown in FIG. 1B. In this position, holder 2 is flush with the top of container 1. The top of container 1 may have an outwardly projecting lip, with a slight taper downward. The lip sits on the ground, with the top substantially flush with the ground, but slightly above the ground due to the lip. The lip keeps the container from sinking deeper into the ground. The taper enables mowing equipment or the like from colliding with the top of the container.

The grave site visitor grabs holder 2 from the bottom at two slots 4 by pinching a tab 6 with his or her fingers to lift holder 2. Then the user turns the holder 2 upright and puts it back into container 1, as shown in FIG. 1A. Tab 6 serves to sit on a projection 7 in a bottom of container 1, so that the holder is above the top of the container for use. One then puts a lit charcoal briquette into the top of the holder 2, extinguishes any flame, and pours or places resin incense onto the briquette.

The top of holder 2 has a concave briquette and incense receiving surface formed by a curved plate 3, preferably metal or other incombustible, durable and easy to clean material, and also has an insulation layer 5 (preferably an air gap insulation but could also contain an insulating material) between curved plate 3 and a remainder of a body of holder 2. The parts may be friction fit together, and/or bonded or glued with a heat resistant and weather resistant epoxy. The parts may also be screwed together, bolted, epoxied, welded, or otherwise fixed together.

At the exterior of the top of the holder, preferably at 180 degrees apart, there are two tabs 9 for handling holder 2. The tabs 9 are preferably of a material that is a good heat insulator and relatively easy to grip, as well as durable, for example, a strong plastic.

When the user is done, the user grabs holder 2 at tabs 9, empties any charcoal or ash or other residue in an appropriate receptacle, and turns holder 2 upside down. The top section (at curved plate 3) of holder 2 fits over projection 7 and into a channel 8 around projection 7. This fit enables the edges of the bottom of the holder to fit flush with the top of the container 1 while the holder is in the storage position of FIG. 1B.

Figure 1E:
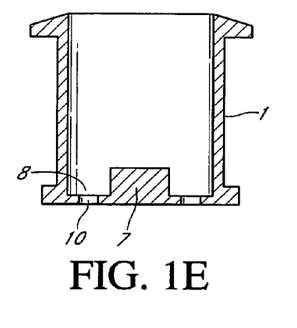
FIG. 1E is a vertical sectional view of the container of FIG. 1A.
Figure 1F:
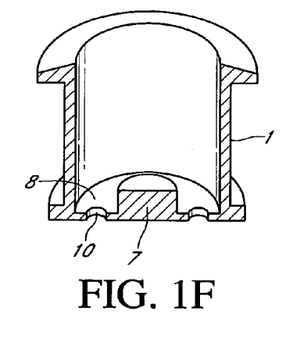
FIG. 1F is a perspective view of the container of FIG. 1A, with the container sliced vertically.

FIGS. 1E and 1F show multiple drain holes 10 in the channel 8 around the projection 7 for rainwater or irrigation water to pass through. A hole or holes may also be provided in projection 7. Alternatively or in addition thereto, the outer edges of the holder, at the bottom thereof, may be made so as to form a relatively water tight seal using a compressible material around the edges of container 1 and/or holder 2.

Figure 2A:
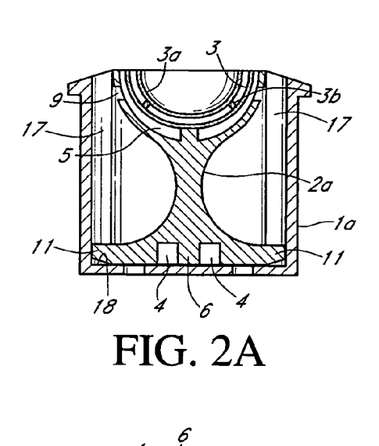
FIG. 2A is a vertical sectional view of an incense holder and container in a use position in accordance with a second embodiment of the invention.
Figure 2B:
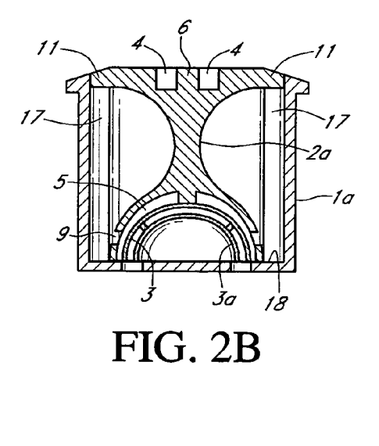
FIG. 2B is a vertical sectional view of the incense holder and container of FIG. 2A in a storage position.
Figure 2C:
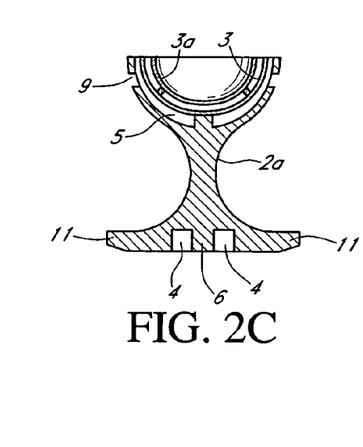
FIG. 2C is a vertical sectional view of the incense holder of FIG. 2A.
Figure 2D:
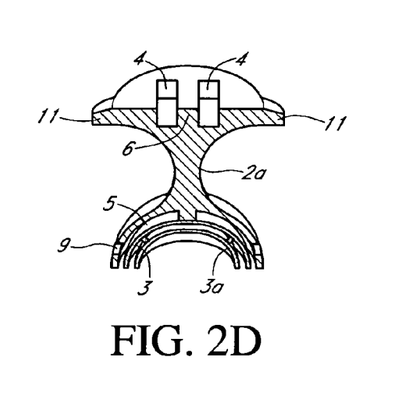
FIG. 2D is a perspective view of the incense holder of FIG. 2A, with the holder sliced vertically, and in the storage position of FIG. 2B.
Figure 2E:
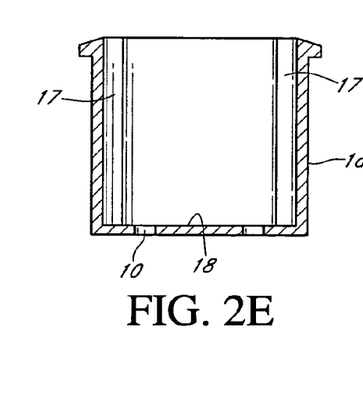
FIG. 2E is a vertical sectional view of the container of FIG. 2A.
Figure 2F:
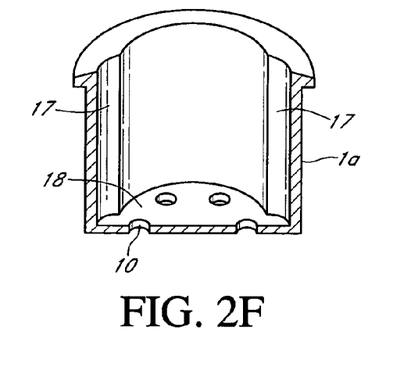
FIG. 2F is a perspective view of the container of FIG. 2A, with the container sliced vertically.
Figure 2G:
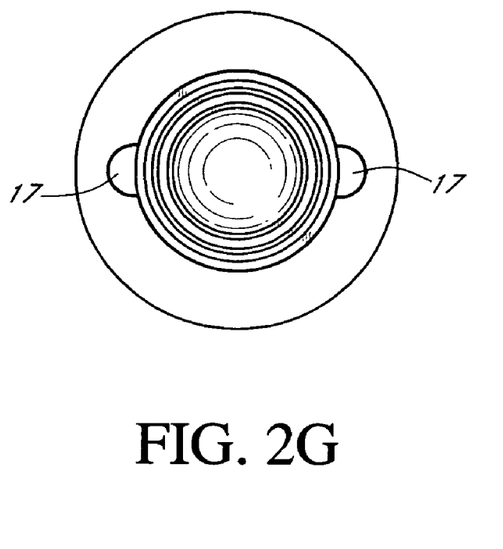
FIG. 2G is a top view of the container and holder in the use position of FIG. 2A.
Figure 2H:
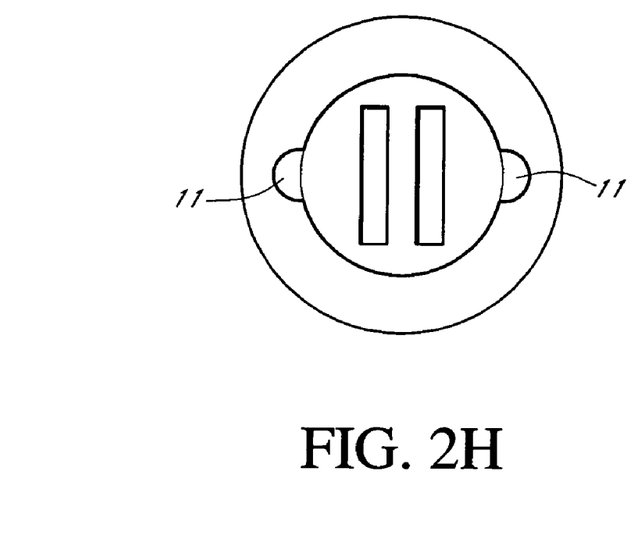
FIG. 2H is a top view of the container and holder in the storage position of FIG. 2B.

FIGS. 2A to 2H show a second embodiment of the incense burner. Holder 2a and container 1a are substantially the same or the same as holder 2 and container 1 of FIGS. 1A to 1F (with like reference numbers representing like elements), except that container 1a has a relatively flat bottom 18 so that when holder 2a is right side up and in container 1a, the top of the holder 2a is flush or substantially flush with the top of container 1a, as best shown in FIG. 2A. This flush fit even in the use position provides added assurance that the holder 2a will not interfere with maintenance of the grave site, even if a user inadvertently leaves the holder in the use position. In addition, there are vertical recesses 17 along the inside of the container 2a from top to bottom thereof, as best shown in FIGS. 2A, 2B, 2E and 2F, so that there is access or clearance for tabs 9 in the top of the holder so a user can pick up the holder 2a if it is in the use position (see FIG. 2G), and projections 11 at the bottom of the holder when the holder is in the storage position (see FIG. 2H). The projections 11 serve to help seal the container when the holder is in the storage position, as shown in FIGS. 2B and 2H, and serve to help center and stabilize the holder in the use position of FIGS. 2A and 2G.

The openings in the bottom of the container also facilitate air flow from removal of the holder, particularly if the bottom of the container is disposed so that there is at least a small clearance before it contacts the ground, or if some small stones or the like are placed in the small clearance, to vertically support the container, yet leave room for air and for drainage.

A further difference between the embodiment of FIGS. 2A to 2H and the embodiment of FIGS. 1A to 1F is that in FIGS. 2A to 2H, there is an additional curved plate 3a above curved plate 3 to provide for further air insulation and air flow between plate 3a, which will hold the incense in this embodiment, and plate 3. Plate 3a may be fixed to plate 3 by bolts 3b, or screws, welding or any other reasonable mechanism. It is also noted that plate 3a may be added to the embodiment of FIGS. 1A to 1F if desired.

Figure 3A:
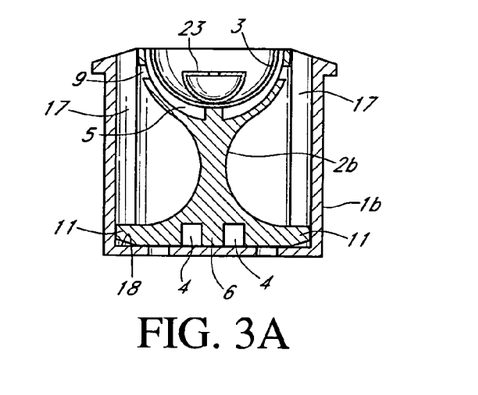
FIG. 3A is a vertical sectional view of an incense holder and container in a use position in accordance with a third embodiment of the invention where the incense holder contains a further holder for stick incense.
Figure 3B:
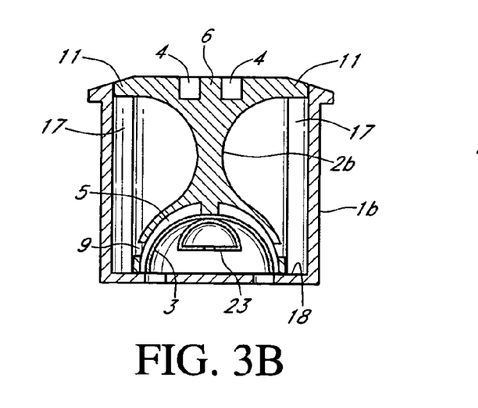
FIG. 3B is a vertical sectional view of the incense holder and container of FIG. 3A in a storage position.
Figure 3C:
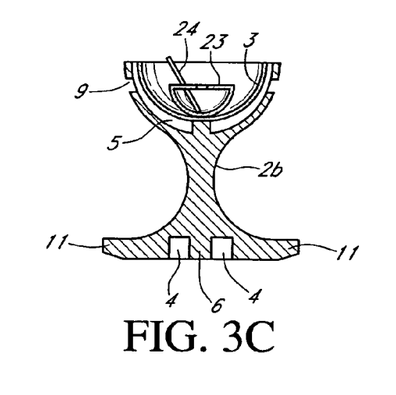
FIG. 3C is a vertical sectional view of the incense holder of FIG. 3A.
Figure 3D:
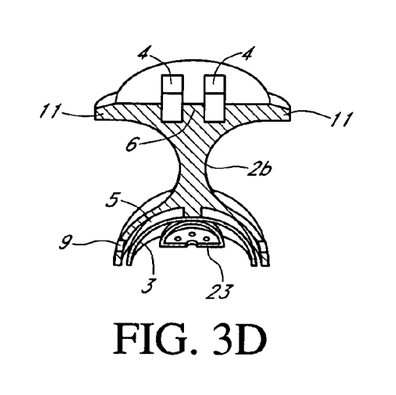
FIG. 3D is a perspective view of the incense holder of FIG. 3A, with the holder sliced vertically, and in the storage position of FIG. 3B.
Figure 3E:
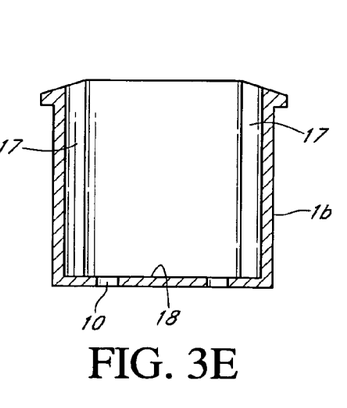
FIG. 3E is a vertical sectional view of the container of FIG. 3A.
Figure 3F:
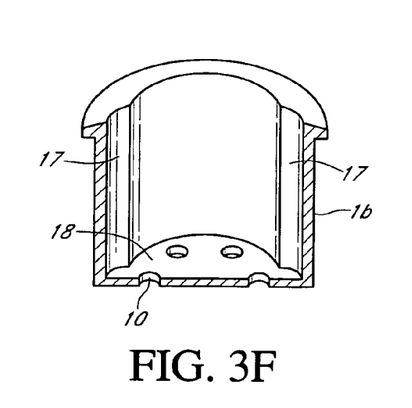
FIG. 3F is a perspective view of the container of FIG. 3A, with the container sliced vertically.
Figure 3G:
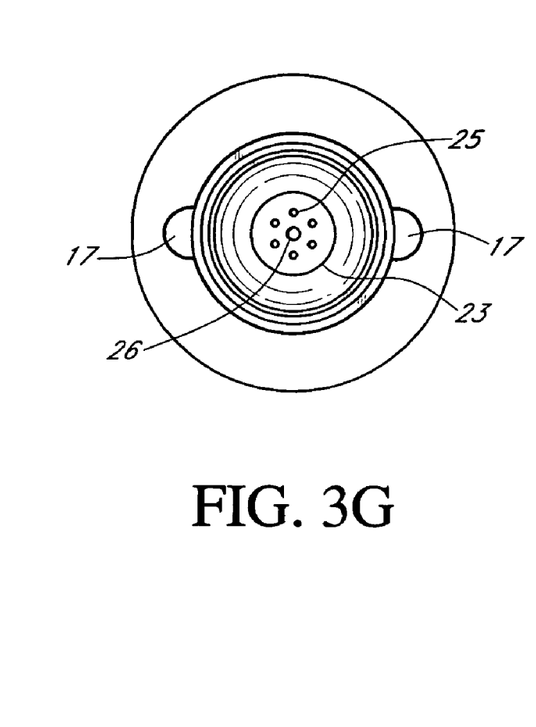
FIG. 3G is a top view of the container and holder in the use storage position of FIG. 3A.
Figure 3H:
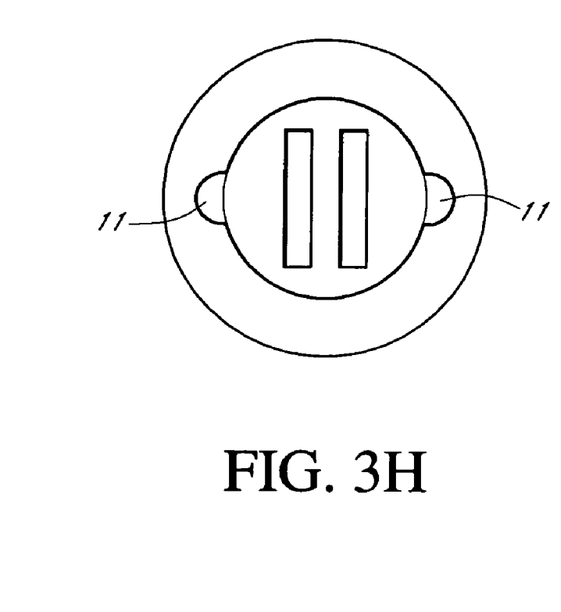
FIG. 3H is a top view of the container and holder in the storage position of FIG. 3B.

With reference to FIGS. 3A to 3H, holder 2b and container 1b are substantially the same or the same as holder 2a and container 1a in FIGS. 2A to 2H (with like reference numbers representing like elements). However, in this embodiment, holder 2b has a stick incense retaining member 23 which is fixed to the inside of the curved plate 3, e.g., by a screw or bolt, welding, or otherwise. Retaining member 23 is shaped to receive one end of a stick incense 24 (FIG. 3C). The stick incense is inserted into the retaining member 23 and is lit. The incense burns within holder 2b. As shown in FIG. 3G, retaining member 23 has small holes 25 for receiving stick incense, and a large central hole 26 for air flow for cooling.

In another embodiment of the invention (not shown), the bottom of holder 2b may be rounded, such as a hemispherical shape, or other nonflat shape, so that the holder will only stand when supported, i.e., within container 1b. This embodiment prevents or at least discourages use of holder 2b outside of container 1b.

The exact mating shapes of the holder and container as shown need not be used. One could use square shapes, hexagons, ellipses, or the like. The holder does not need to mate with the container all the way around the periphery of the bottom of the holder, but preferably does or is close to the same size as the interior of the container, to minimize entry of dirt, water, and other debris, such as leaves, grass cuttings, and the like. Preferably, the container and holder have a relatively small vertical height, and also a relatively small footprint but large enough to accommodate a typical charcoal briquette.

Figure 4:
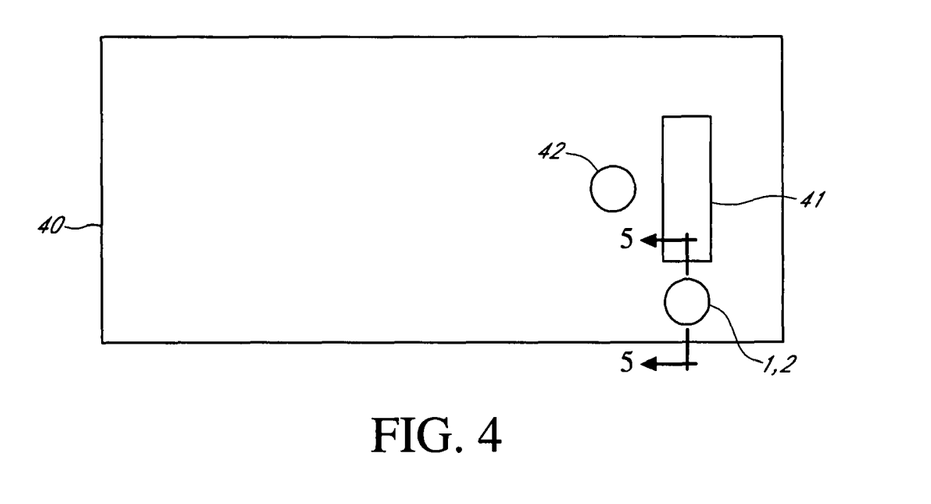
FIG. 4 is a top, schematic view of a grave site, with a marker, a vase and a container and holder in accordance with an embodiment of the invention.
Figure 5:
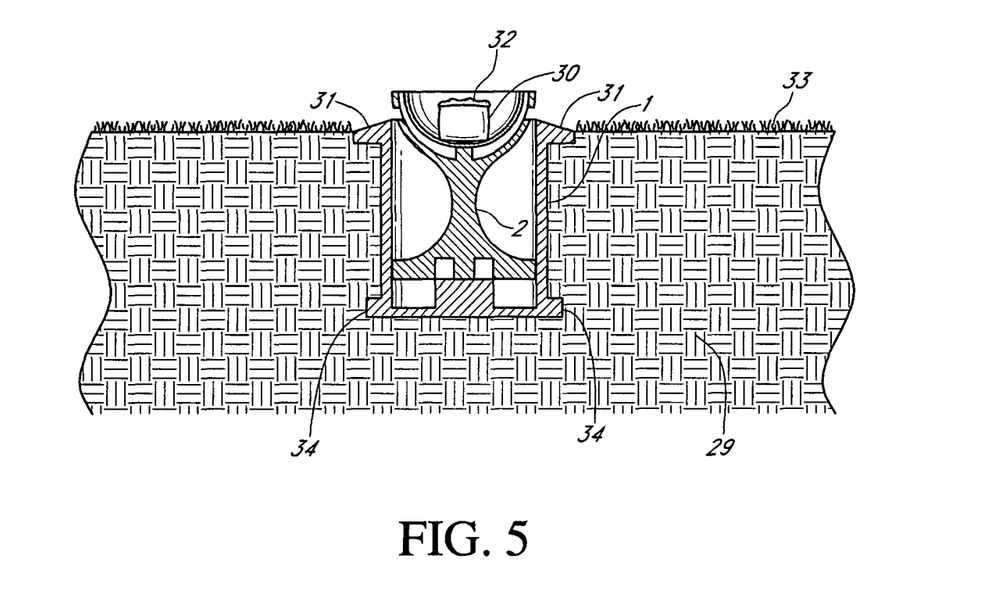
FIG. 5 is a partial vertical sectional view of the grave site, container and holder, taken along a line 5-5 of FIG. 4, with the holder in a use position and with charcoal and incense therein.

As shown in FIG. 4, container 1 and holder 2 may be located in the ground at a grave site 40, and, e.g., adjacent a grave marker 41 or headstone. There may also be an in ground vase 42. As shown in FIG. 5, container 1 and holder 2 are of any of the above embodiments of the invention, e.g., of FIG. 1A, and are located in dirt 29. Container 1 has a top rim 31 which sits on a portion of the dirt 29 or other ground surface or adjacent the surface, to keep the container from sinking into the ground. A bottom rim 34 has dirt 29 over it, to help keep the container in the ground. Grass 33 typically is growing on grave site 40.

As noted above, with holder 2 in the use position, a charcoal briquette 30 is placed in the holder, and is lit, and incense 32 is placed or poured onto the briquette, to burn the incense.

Figure 6:
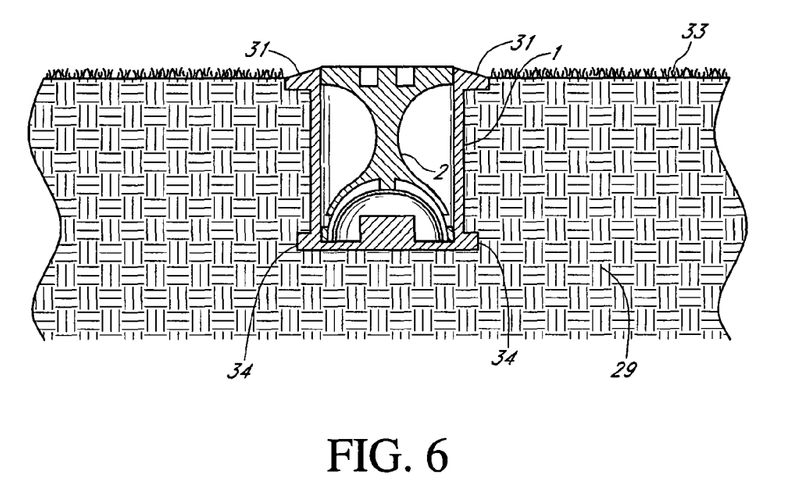
FIG. 6 is a view similar to FIG. 5, with the holder in the storage position.

FIG. 6 is similar to FIG. 5, but with the holder in the upside down, storage position, so that it is flush or substantially flush with the ground at grave site 40.

Figure 7:
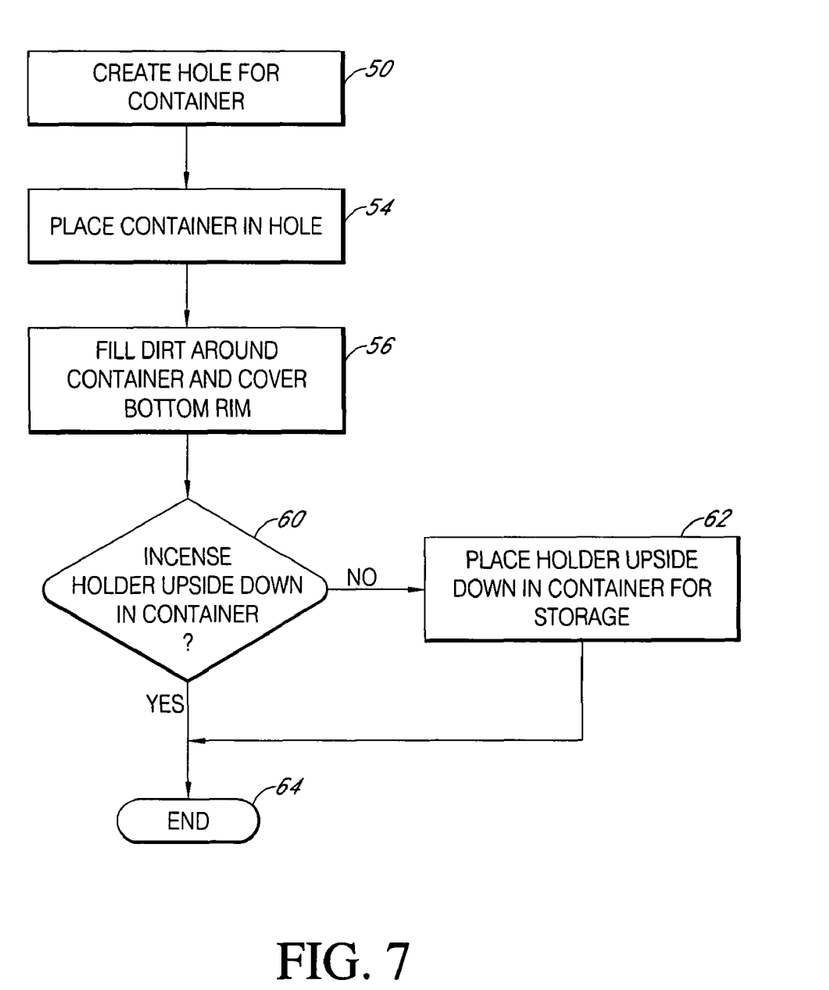
FIG. 7 is a flow diagram of a method for installing a container and holder in accordance with a preferred embodiment of the invention.

The method of installation of the container and holder already clear to one of ordinary skill from the above is nonetheless shown schematically in FIG. 7. First, at step 50, one creates a hole in the grave site of sufficient size to insert the container. At step 54, the container is placed in the hole. At step 56, dirt is filled around the container, such that the bottom rim is covered.

At step 60, if the holder is already in the container, and upside down, then installation ends at step 64. If the holder is not already in the container upside down, then the holder is placed upside down in the container at step 62, and installation ends at step 64.

Figure 8:
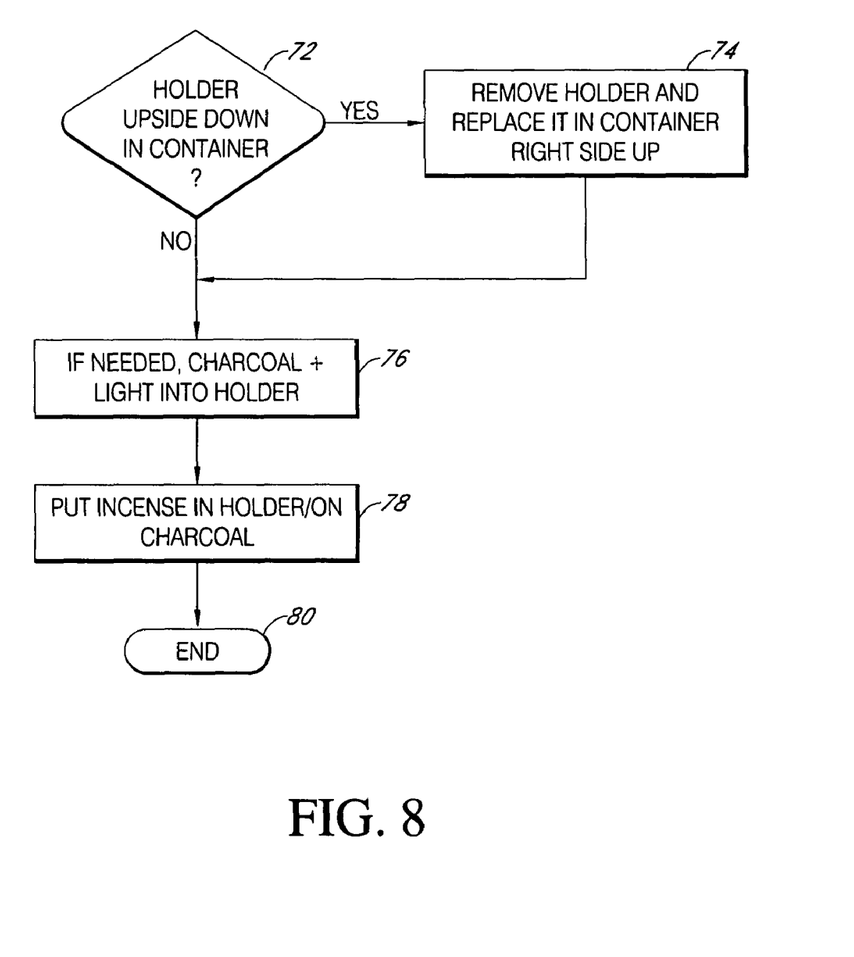
FIG. 8 is a flow diagram of a method for using the container and holder to burn incense in accordance with another preferred embodiment of the invention.

In FIG. 8, the process of using the incense burner, though evident from the above, is shown schematically. First, a grave visitor arrives at the grave site at step 70. If the visitor sees that the holder (of any embodiment) is upside down in the storage position (at step 72), then he or she removes the holder and replaces it in the container right side up for use (step 74). If the holder is already right side up (step 72), or after placing the holder right side up (step 74), if needed charcoal is placed into the holder and lit (or already lit) at step 76. At step 78, incense is placed in the holder and/or on the charcoal so that it burns, or stick incense is placed in the holder. Then, the process ends at step 80.

Although the invention has been described using specific terms, devices, and/or methods, such description is for illustrative purposes of the preferred embodiment(s) only. Changes may be made to the preferred embodiment(s) by those of ordinary skill in the art without departing from the scope of the present invention, which is set forth in the following claims. In addition, it should be understood that aspects of the preferred embodiment(s) generally may be interchanged in whole or in part.

What is claimed is:

1. A cemetery incense burner comprising:
a removable resin incense holder; and
a container having a top and bottom and for accommodating the holder, wherein the holder is vertically slidable within the container, wherein the holder has a top section comprising an outer body, an insulation layer and a concave plate, the insulation layer being disposed between the outer body and the concave plate, wherein the container is substantially cylindrical and has a protruding member in the bottom center to support the removable incense holder when the holder is in a use position with the concave plate facing up and away from the container such that the top section of the holder is above the top of the container and above the surface of the ground while it is being used as a censer, and wherein there are vertical recesses in an inner side wall of the container that extend substantially from the top of the container to the bottom and the holder has two tabs extending outwardly at approximately 180 degrees for fitting in the recesses in the container.

2. The cemetery incense burner of claim 1 wherein the two tabs are for grasping the holder.

3. The cemetery incense burner of claim 1 wherein a bottom of the holder has a tab for grasping the holder.

4. The cemetery incense burner of claim 1 wherein the bottom surface of the removable incense holder mates with the top of the container to substantially seal the container when the removable incense holder is in a storage position with the concave plate facing down and into the container.

5. The cemetery incense burner of claim 1 wherein an inner surface of the bottom of the container is flat and the top of the holder and the top of the container are substantially flush with each other.

6. The cemetery incense burner of claim 1 wherein the insulation layer comprises air.

7. The cemetery incense burner of claim 4 wherein the container comprises openings in the bottom thereof to facilitate air flow during the withdrawal and insertion of the holder.

8. The cemetery incense burner of claim 1 wherein the holder further comprises means for retaining stick incense disposed in the concave plate.

9. A cemetery incense burner in combination with ground at a grave site, the combination comprising:
ground at a grave site;
a container having a top and a bottom and being installed in the ground at the grave site with the top substantially flush with a surface of the ground at the grave site; and
a removable resin incense holder disposed in the container wherein the holder has a top section comprising an outer body, an insulation layer and a concave plate, the insulation layer being disposed between the outer body and the concave plate, wherein the concave plate is for receiving a piece of charcoal and incense and wherein the container is substantially cylindrical and has a protruding member in the bottom center to support the removable incense holder when the holder is in a use position with the concave plate facing up and away from the container such that the top section of the holder is above a top of the container and above the surface of the ground while it is being used as a censer and wherein there are vertical recesses in an inner side wall of the container that extended substantially from the top of the container to the bottom and the holder has two tabs extending outwardly at approximately 180 degrees for fitting in the recesses in the container.

10. The combination of claim 9, wherein the holder may be inserted upside down or right side up in the container, and the container having openings in the bottom thereof to facilitate air flow during the withdrawal and insertion of the holder, and wherein the container and holders mate so as to form a seal with the holder in the upside down position in the container.

11. The combination of claim 9, wherein the concave plate has a portion for retaining stick incense disposed therein.

12. A cemetery incense burner comprising:
- an incense holder wherein the holder has a top section comprising an outer body, an insulation layer and a concave plate, the insulation layer being disposed between the outer body and the concave plate; and
- a container having a top and bottom and for receiving the holder in a position with the top facing upward, wherein the container is also adapted for being turned upside down for removably receiving the incense holder in a position with the top section of the holder facing downward and adjacent a bottom of the container, and wherein the container and holders mate so as to form a seal with the holder in the upside down position in the container, and the container having openings in the bottom thereof to facilitate air flow during the withdrawal and insertion of the holder.

13. The combination of claim 9, wherein the insulation layer comprises air.

14. The cemetery incense burner of the claim 12, wherein the insulation layer comprises air.

15. A cemetery incense burner comprising:
- a removable resin incense holder; and
- a container having a top and bottom and for accommodating the holder, wherein the holder is vertically slidable within the container, wherein the holder has a top section comprising an outer body, an insulation layer and a concave plate, the insulation layer being disposed between the outer body and the concave plate, wherein the container and holder mate so as to form a seal with the holder in a position when the top section including the concave plate for receiving incense is face down in the container for storage.

* * * * *